United States Patent
Jensen et al.

[11] Patent Number: 5,951,583
[45] Date of Patent: Sep. 14, 1999

[54] THROMBIN AND COLLAGEN PROCOAGULANT AND PROCESS FOR MAKING THE SAME

[75] Inventors: Todd L. Jensen, St. Paul, Minn.; Gary Gershony, Alamo, Calif.

[73] Assignee: Vascular Solutions, Inc., Plymouth, Minn.

[21] Appl. No.: 09/031,847

[22] Filed: Feb. 27, 1998

Related U.S. Application Data

[63] Continuation-in-part of application No. 08/850,477, May 5, 1997, Pat. No. 5,868,778, and application No. 08/877,255, Jun. 17, 1997, which is a continuation of application No. 08/549,430, Oct. 27, 1995, which is a continuation-in-part of application No. 08/303,088, Sep. 8, 1994, abandoned, which is a continuation of application No. 08/067,213, May 25, 1993, Pat. No. 5,383,896, said application No. 08/850,477, is a continuation of application No. 08/549,332, Oct. 27, 1995, Pat. No. 5,626,601.

[51] Int. Cl.$^6$ .................................................. A61M 29/00
[52] U.S. Cl. ............................ 606/194; 604/96; 530/383
[58] Field of Search .................................. 606/194, 213; 604/96, 101; 424/145.1; 530/383

[56] References Cited

U.S. PATENT DOCUMENTS

| | | | |
|---|---|---|---|
| 5,843,442 | 12/1998 | Soule et al. | 424/145.1 |
| 5,861,382 | 1/1999 | Cohen et al. | 530/383 |

*Primary Examiner*—Michael Buiz
*Assistant Examiner*—Kevin Truong
*Attorney, Agent, or Firm*—Patterson & Keough, P.A.

[57] ABSTRACT

A procoagulant designed to effect hemostasis at a puncture site in a patient's vasculature without the aid of manual compression is comprised of lyoplilized thrombin that is reconstituted with a buffered diluent and collagen that is mixed with the reconstituted thrombin to produce a viscous mixture. The buffered diluent is preferably of sodium phosphate and water. The procoagulant is essentially isotonic and has a pH in the range of 5–10. The method of making the procoagulant is comprised of the steps of reconstituting the lyophilized thrombin with the buffered diluent and then, mixing the reconstituted thrombin with collagen to both reduce the size of the particles of the collagen and form a fluid mixture.

2 Claims, 1 Drawing Sheet

THROMBIN AND COLLAGEN PROCOAGULANT AND PROCESS FOR MAKING THE SAME

Continuation-in-Part of application Ser. No. 08/850,477, filed May 5, 1997 now U.S. Pat. No. 5,868,778, which is a continuation of application Ser. No. 08/549,332, filed Oct. 27, 1995, now U.S. Pat. No. 5,626,601, issued May 6, 1997. This is also a continuation in part of application Ser. No. 08/877,255, filed Jun. 17, 1997 now pending, which is a continuation of application Ser. No. 08/549,430, filed Oct. 27, 1995 now pending, which is a continuation in part of application Ser. No. 08/303,088, filed Sep. 8, 1994 now abandoned, which is a continuation application of application Ser. No. 08/067,213, filed May 25, 1993, now U.S. Pat. No. 5,383,896, issued Jan. 24, 1995.

FIELD OF THE INVENTION

This invention relates to procoagulants and more particularly to a procoagulant for effecting hemostasis at a puncture site of the vascular system.

BACKGROUND OF THE INVENTION

Achieving rapid and effective closure of surgical sites has attracted considerable attention throughout history. In more recent times, the proliferation of technological advances has resulted in the ability to access various parts of the human anatomy not previously contemplated. One example of this relates to the diagnostic and surgical use of the vasculature, and the attendant desire for prompt closure of such access sites. Examples of such percutaneous procedures include recanalization of atherosclerotic blood vessels, such as balloon angioplasty or artherectomy, cardiac mapping and treatment, placement of aortic balloon pumps, and other procedures. In recent years, both the types and numbers of such procedures utilizing percutaneous access to blood vessels have increased greatly.

These types of procedures generally involve the puncture of a blood vessel with a thin walled needle. A guidewire is then often placed through the needle into the blood vessel and the needle is withdrawn. An intravascular sheath is then advanced over the guidewire and into the lumen of the vessel. The sheath is then used as an ingress/egress means during the procedure, and is known generally as an introducer sheath. Following completion of the procedure, the introducer sheath may be removed, but this requires the application of prolonged manual pressure over the puncture site by a physician or other suitably trained medical personnel, as well as the use of other compression devices (e.g. sandbags) after manual compression is done. The time involved is extensive and costly. Also, patients are often treated with a variety of anticoagulant and thrombolytic agents, particularly in the setting of unstable angina or myocardial infarction. The discomfort and delay in mobilization and attendant morbidity, both physical and psychological, for patients is significant. This need for ongoing compression (usually 8–12 hours) frequently prolongs hospital stays and adds cost to the patient and society in general.

Alternatively, the sheath may be left in the puncture site for a prolonged period of time until the patient's coagulation status has returned to normal. Depending on the size of the vascular sheath, there may be an increased risk of bleeding to the patient, which may even require blood transfusion with its known attendant risks. In addition, there is a significant risk of injury to the blood vessel upon removal of the sheath, particularly if the sheath has been in place for a prolonged period of time. This includes the possible development of a pseudo-aneurysm or severe hematoma.

In view of the above, there is a need for a system and method that can effect hemostasis of a puncture site quickly, safely, and within patient comfort ranges. Such system and method ideally would effect this closure without the need for manual compression, other compression devices, or suturing at the surgical site.

It is known to place procoagulants, tissue adhesives, or similar materials at puncture sites or other surgical locations to facilitate hemostasis. See, for example, Pfab, et al., "Local Hemostasis of Nephrostomy Tract with Fibrin Adhesive Sealing in Percutaneous Nephrolithotomy," *European Urology*, vol. 13, pp. 1 18–21, 1987 (fibrin); Abbott, et al., "Microcrystalline Collagen as a Topical Hemostatic Agent for Vascular Surgery," *Surgery*, vol. 75, no. 6, pp. 926–33, Jun. 1974 (collagen); and Lunderquist, et al., "Transhepatic Catheterization and Obliteration of the Coronary Vein in Patients with Portal Hypertension and Esophageal Varices," *The New England Journal of Medicine*, vol. 291, no. 13, pp. 646–49, Sep. 26, 1974 (thrombin). Numerous other references describe use of such hemostatic agents for various purposes, in various combinations, and with certain other materials. For example, it is quite well known to use a collagen based fleece plug or tampon to seal a percutaneous access site. See, e.g., Krause, et al., "Utility of a Percutaneous Collagen Hemostasis Device: To Plug or Not to Plug?," *Journal of the American College of Cardiology*, vol. 25, no. 7, pp. 1685–92. June 1995.

Other combinations of materials are known for use in wound closure, such as in U.S. Pat. No. 4,453,939 titled "Composition for Sealing and Healing wounds" in winch a collagen carrier is coated with a mixture of a fibrinogen component, and thrombin component, and optional additional additives to promote the infiltration and growth of fibroblasts. Sheets or coatings are similarly well known for closing wounds by promoting coagulation of blood using thrombin, collagen, fibrin and related products, as described in U.S. Pat. No. 4,683,142. In many references, the components are in powdered or lyophilized form, for example as in U.S. Pat. No. 4,515,637 titled "Collagen-Thrombin Compositions." In this patent, the collagen product is readily absorbable when placed in vivo, and is storage stable. This latter issue of thrombin stability has generally been problematic, and has led to select oil of lyophilized rather than reconstituted thrombin to achieve long term stability.

The embodiments of either powdered, lyophilized, paste, tampon or solid type of hemostatic agents are inadequate for achieving certain advantages in closure of access sites in a patient's vasculature. Indeed, even a liquid or aqueous composition useful for promoting hemostasis in certain applications might be inadequate for such specialized purposes as discussed below. One such example is found in U.S. Pat. No. 5,290,552, titled "Surgical Adhesive Material," in which is described a surgical adhesive in an aqueous composition having fibrinogen, FXIII, collagen, thrombin, $Ca^2$, and an optional antifibrinolytic agent. The material is formed from the patient's plasma thus avoiding the difficult challenges of determining proper reagents for concentration or isolation of the fibrinogen. Avoidance of solid forms of hemostatic materials is also an advantage to certain compositions, such as those in an aqueous, gel, or paste form. Such structural forms allow for packing or molding of the hemostatic material to achieve better conformity with the cavity or wound to be healed.

In U.S. Pat. No. 4,891,359, titled "Hemostatic Collagen Paste Composition," a paste or dough mixture comprises 5 to 30% of a water insoluble crosslinked collagen powder of 10 to 100 mesh particle size and 70 to 95%, of water or an aqueous saline solution. In one embodiment, an aqueous glycerine solution containing a hemostatic enhancing amount of thrombin is added, with the resulting paste having a consistency suitable for packing into a squeeze tube or syringe package. Various additives may be employed to enhance pH compatibility and to prolong the stable life of the thrombin in the paste composition.

Other references are known which address ways to prepare gels as drug delivery vehicles onto the skin or into a body cavity of a mammal, such as in U.S. Pat. Nos. 5,437,292, 5,298,260 and 5,292,516. In U.S. Pat. No. 5,437,292 a gel which contains fibrinogen and thrombin is designed to be packed around a blood vessel or organ, with a compression of the gel proximally provided to prompt closure of a puncture site. In U.S. Pat. No. 5,298,260, a thermoreversible drug carrying gel is formed for topical use on, for example, a burned portion of a patient's skin. In one embodiment, the gel would have characteristics of a pH about 7 and an osmolality of about 650 mOsm/kg in the liquid state, and then upon thermal transition to a gel the material would be at a pH of about 7 and an osmolality of about 290 mOsm/kg. While the reference contains no suggestion of using the gel material for a non-thermal reversible hemostasis application, there is disclosure of certain desirable attributes of the final product form.

Similarly, in U.S. Pat. No. 4,592,864, an aqueous atelocollagen solution is disclosed. This solution is designed for injection into living bodies as a means of regenerating collagen fiber, and is a syringe injectable fluid under the pH and osmolality conditions close to those in living bodies, and which forms collagen fiber when equilibrated with biological conditions after injection. This product is designed to be injected into ruptured tissues to fill the area of the rupture without incision. A sodium phosphate buffer is used to control the pH and osmolality of the solution so that at room temperature the solution remains as a liquid and once injected into a living organism the solution quickly regenerates collagen fiber.

Although many uses of the above hemostatic materials are disclosed, and many types of such materials are used in connection with closure of vascular access sites, no combination exists which provides an injectable liquid solution procoagulant as described below, for the specific uses as described below, and which achieves the advantages discussed.

SUMMARY OF THE INVENTION

A flowable and syringe injectable procoagulant is designed to effect hemostasis at a puncture site in a patient's vasculature without the aid of manual compression and is comprised of lyophilized thrombin which is reconstituted with a buffered diluent, and collagen that is mixed with the reconstituted thrombin to produce an aqueous mixture. The buffered diluent is preferably comprised of sodium phosphate and water. The procoagulant is relatively low osmolality, in a preferred range of about 250 to about 430 mOsm/kg and has a pH in the range of about 5–10. The method of making the procoagulant comprises the steps of reconstituting the lyophilized thrombin with the buffered diluent and then mixing the reconstituted thrombin with collagen to form a mixture that is within optimal patient ranges for pH, osmolality, and patient comfort.

RELATED APPLICATIONS

This is a continuation in part of U.S. patent application Ser. No. 08/850,477, filed May 5, 1997, which is incorporated herein in its entirely, and which is a continuation of U.S. patent application Ser. No. 08/549,332, filed Oct. 27, 1995, now U.S. Pat. No. 5,626,601, issued May 6, 1997. This is also a continuation in part of U.S. patent application Ser. No. 08/877,255, filed Jun. 17, 1997, which is a continuation of application Ser. No. 08/549,430, filed Oct. 27, 1995, which is a continuation in part of application Ser. No. 08/303,088, file Sep. 8, 1994, which is a continuation application of application Ser. No. 08/067,213, filed May 25, 1993, now U.S. Pat. No. 5,383,896, issued Jan. 24, 1995.

DETAILED DESCRIPTION OF THE INVENTION

Figure 1:
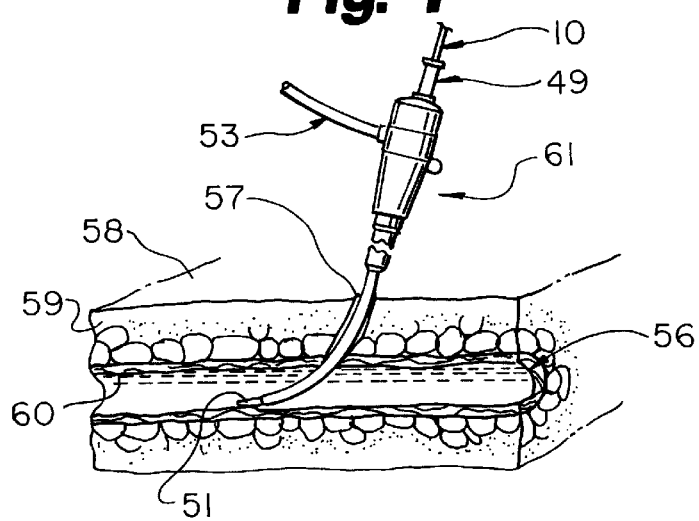
FIG. 1 is a view of a vascular sealing device inserted through an introducer sheath and into a patient's vascular system, which is shown in enlarged and in section.

The invention relates to means for effecting closure of a puncture or other opening in a blood vessel or other body cavity which has been entered through percutaneous techniques. In one embodiment, the procoagulant is introduced through a percutaneous vascular introducer of a vascular sealing device to a vascular puncture site. Alternatively, the procoagulant may be introduced through an additional lumen and apertures. In one embodiment, the puncture site is temporally sealed by inflatable means positioned within the blood vessel lumen, and the procoagulant is then accurately deposited at the external vessel wall proximal to the puncture and the inflatable means. After a brief period of time, the inflatable means is deflated and withdrawn proximally through the volume of procoagulant as the latter is coagulating.

At the time of initial percutaneous deposition of the procoagulant the inflatable means prevents the procoagulant from entering the lumen of the blood vessel. However, due to the rapid coagulation and excellent localization of this procoagulant, the inflatable means may be safely removed from the site in only a very short period of time. This obviates the need for excessive compression, for placement of solid plugs in the wound, or for any ligatures or the like at the already sensitized tissue site. Such a procedure facilitates rapid ambulation and its attendant benefits.

In one embodiment, a thrombin and collagen procoagulant comprises a mixture of collagen and thrombin a buffered diluent. This mixture allows for the enzymatic action of thrombin on the blood clotting process to create a vascular seal at the arteriotomy site. The collagen is preferably a commercial product known as AVITENE, and is manufactured by Davol, Inc. This material is PMA approved for the purpose of enhancing hemostasis in various surgical applications. The thrombin is preferably Thrombin-JMI and is manufactured by GenTrac Incorporated, a subsidiary of Jones Medical Industries. The thrombin material is also PMA approved for the purpose of enhancing hemostasis in various surgical applications.

It is appreciated that the collagen and thrombin enhance the blood clotting process, however, they each do this by very different mechanisms. Thrombin is a serine protease which enzymatically cleaves circulating fibrinogen to allow it to form a fibrin clot. Collagen, however, enhances the hemostatic process by activating platelets. The activated platelets form an initial hemostatic plug in addition to playing a role in the activation of proteins in the clotting cascade. A second important role of the collagen within the procoagulant is to increase the viscosity of the suspension that is applied to the arteriotomy site. In other words, the collagen helps to maintain the procoagulant mixture at the location it is initially applied and minimizes any dilution the procoagulant would otherwise experience.

As will be further appreciated, the complex interaction of the constituent materials of the preferred procoagulant necessitated considerable experimentation to optimize, and such was not clearly possible without several critical developments. For example, at least four iterations were necessary to develop the preferred embodiments of the invention. These iterations and the final preferred embodiments will be described below. Much of the changes implemented in the procoagulant were in the diluent used to reconstitute the thrombin and the optimization of the mixture for patient receptiveness and efficacy.

A first step in the preparation process involves using a diluent to reconstitute the lyophilized thrombin. A second step in the process involves mixing the reconstituted thrombin with the collagen in a pre-filled syringe by using two syringes connected with a mixing luer.

Procoagulant I

A first iteration of the preferred procoagulant design comprised use of a glass syringe containing 500 mg, of collagen, a 20,000 unit vial of thrombin, and a bottle of 0.9% saline. The saline was provided by the manufacturer of the thrombin and was intended to be the diluent for that product. The procoagulant preparation involved using 10 ml of saline to reconstitute the thrombin. This solution was then mixed with the collagen in a glass syringe. However, it was discovered through stability studies on the procoagulant, that this formulation resulted in very poor stability of the thrombin in the procoagulant. Specifically, the pH of the procoagulant was found to be approximately 3.3, which completely inactivated the thrombin in less than 30 minutes.

When the thrombin was reconstituted in the 0.9% saline the pH was approximately 6.4. However, when the thrombin solution was mixed with the collagen the pH fell to 3.3. This resulted from the acidic nature of the AVITENE collagen which contains residual hydrochloric acid used to extract the collagen from animal tissue. In view of these results, it became clear that the diluent needed to contain some kind of buffering agent to help preserve the activity of the thrombin.

Procoagulant II

A second iteration of the procoagulant design comprised a glass syringe containing 500 mg, of collagen, a 20,000 unit vial of thrombin, a bottle of 0.9% saline and a bottle of sodium phosphate. In order to provide some buffering capacity for the diluent, 0.5 ml of the sodium phosphate, manufactured by Fujisawa, was added to 20 ml of the 0.9% saline. The procoagulant preparation used 10 ml of the sodium phosphate buffered saline to reconstitute the thrombin. This solution was then mixed with the collagen in a glass syringe. The final pH of this procoagulant mixture was approximately 5.0. This formulation was then utilized in human trials.

During the human trials it was discovered that the functional performance of the procoagulant was highly effective, however, there were some patients that complained of significant pain at the puncture site when the procoagulant was administered. In addition, it was learned that the volume of procoagulant utilized was more than twice the amount needed to achieve good hemostasis.

Procoagulant III

A third iteration of the procoagulant involved altering Procoagulant III by reducing the amounts of all the materials used to make the procoagulant by 50% so that the final volume was one-half the initial volume. Specifically, the amount of collagen was reduced from 500 mg to 250 mg. The thrombin was reduced from 20,000 units to 10,000 units, and the diluent was reduced from 10 ml to 5 ml.

Another change involved a modification to the formulation of the diluent as a result of the human pain issue. Investigation into the possible sources of the discomfort suggested the osmolality of the procoagulant. Reasons leading to this suggestion included a calculation of the osmolality of the second iteration, eg., Procoagulant II noted above, which indicated that the procoagulant was very hypertonic. Further investigation suggested that the subcutaneous injection of hypertonic solutions could lead to pronounced pain. Also, animal studies identified tissue necrosis at the site of the procoagulant injection consistent with physiologic response to a hypertonic solution.

In order to determine the actual osmolality and investigate possible alternative buffer formulations, various procoagulant samples were prepared and tested for osmolality level. It was confirmed that the second iteration (Procoagulant II) used in the initial human trials was extremely hypertonic with the osmolality ranging from 840–872 mOsm/kg.

The results of this investigation also suggested that an alternative approach to the buffer formulation could be to replace the 0.9% saline with sterile water for injection. Upon replacing the 0.9% saline with sterile water for injection, the resulting osmolality was lowered to 578 mOsm/Kg. Reducing the quantities of each of the elements also resulted in yet a lower osmolality as it was discovered that there was less salt or solute in the 10,000 unit thrombin vial than in the 20,000 unit thrombin vial.

Thus, the third iteration of the procoagulant design comprised 250 mg of collagen in a glass syringe, a 10,000 unit vial of thrombin and a diluent which comprised a mixture of sodium phosphate and water prepared by adding 0.5 ml of the concentrated sodium phosphate (Fujisawa) to 20 ml of water (also provided by Fujisawa) for injection. The third iteration of the procoagulant preparation involved using 5 ml of the sodium phosphate and water mixture to reconstitute the thrombin. This solution was then mixed with the collagen in a glass syringe. The osmolality of this solution was 477 mOsm/Kg, while the pH was approximately 5.0.

Procoagulant IV

A fourth iteration of a preferred procoagulant design utilizes a specific sodium phosphate buffer which is in the form of a single 5 ml bottle of 35 mM sodium phosphate which is specifically manufactured for the assignee in this case, Vascular Solutions, Inc., by Bioserv Corporation of San Diego, Calif. Procoagulant IV was prepared with 250 mg of collagen in a glass syringe, a 10,000 unit vial of thrombin and the 5 ml bottle of 35 mM sodium phosphate. The 5 ml of 35 mM sodium phosphate is used to reconstitute the thrombin. This solution is then mixed with the collagen in a glass syringe.

The single bottle formulation of 5 ml of 35 mM sodium phosphate improved the ease of use of use of the procoagulant by virtually eliminating the possibility that the user will make an error in the preparation of the diluent and the procoagulant; the single ready-to-use bottle requires no measurements or transfers of fluids to prepare the diluent. Further, in the mixing protocols of the other embodiments of the procoagulant, a double luer connector was used to connect the two syringes containing the collagen and the thrombin solution. This resulted in a number of occasions where the procoagulant plugged a small hole in the side arm of an introducer sheath being used to administer the procoagulant to the patient.

Accordingly, a new method of mixing was developed. The new method involves the addition of a connecting piece between the syringes for the constituent materials. This new piece has about a 1 mm aperture at one end and as such, by pushing the procoagulant through the aperture, the size of the collagen particles are reduced so that they no longer have the tendency to plug the introducer sheath.

Another advantage of Procoagulant IV related to the desire to lower the osmolality even further from that of other embodiments; for example Procoagulant III had a hypertonic osmolality of 477 mOsm/Kg. The final iteration of the procoagulant, using the new buffering system, produced a more preferable osmolality in the approximate range of 420–430 mOsm/Kg.

Another reason for the diluent change was the desire to raise the pH of the procoagulant mixture. The third embodiment of the procoagulant had a pH of approximately 5.0 while the subsequent embodiment had a pH of approximately 6.0 to 6.1. In view of thrombin having a working pH range of 5–10, with an optimum of about 8.5, the latter embodiment of the procoagulant is closer to the optimal pH for thrombin.

Although not readily appreciated, the pH of Procoagulant IV allows the mixture to experience an initial decrease of 20–25% in measured thrombin activity after a one hour time period from initial mixture, up to an additional 5% decrease in thrombin activity in the one to six hour period, and up to an additional 10% decrease in an overall twenty-four hour time period. As such, the Procoagulant IV is active for at least a twenty-four hour effective period.

Exemplary Preparation of An Embodiment

Preparation of a preferred procoagulant is as follows: (1) using a syringe, one vial of 10,000 unit thrombin is reconstituted with 5 ml volume of 35 mM phosphate buffered saline; (2) the needle of a 10 ml plastic syringe is inserted into the reconstituted vial of thrombin and 5 ml of the thrombin solution is withdrawn into the syringe, and the needle is then withdrawn from the vial, removed and discarded; (3) the plunger on a 10 ml glass syringe containing collagen, with attached mixing luer and male cap, is depressed until the collagen is compressed to 2–3 ml (the collagen must be compressed to 2–3 ml in the syringe to allow proper mixing); (4) the male cap is removed from the mixing luer on the collagen syringe and the 10 ml syringe containing the reconstituted thrombin is attached to the mixing luer on the glass syringe containing collagen; (5) all of the reconstituted thrombin is pushed from the 10 ml syringe into the glass syringe; (6) no more than 4 ml of the collagen/thrombin mixture is pushed into the 10 ml syringe (the entire contents of the collagen/thrombin mixture should not be pushed into the 10 ml syringe at this time as thorough mixing may be impeded); (7) the 4 ml of the collagen/thrombin mixture is returned to the 10 ml glass syringe; (8) the entire volume of the collagen/thrombin mixture is pushed between the two syringes; (9) about ten complete exchanges of the collagen/thrombin mixture are performed between the syringes to ensure a homogeneous mixture; (10) with all of the procoagulant solution in the 10 ml syringe, the 10 ml glass syringe is detached and discarded. The procoagulant is now ready for delivery to the puncture site by any appropriate delivery means.

Trials

Figure 2:
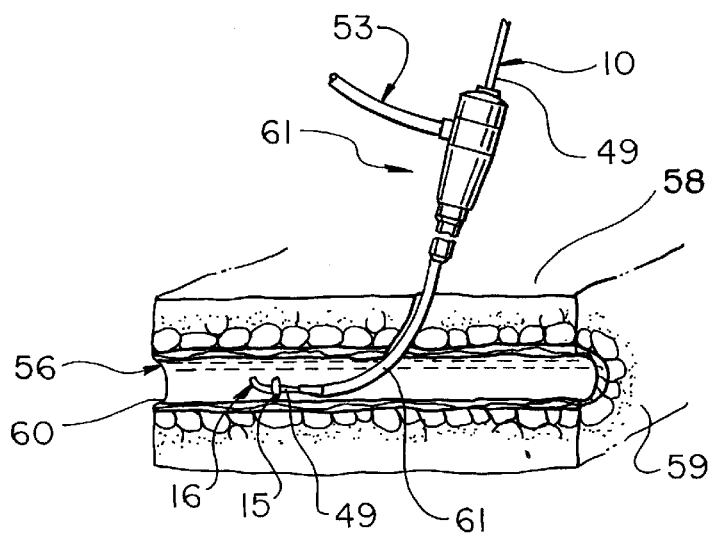
FIG. 2 is a view of the vascular sealing device inserted through a vascular introducer or sheath, and being inflated.
Figure 3:
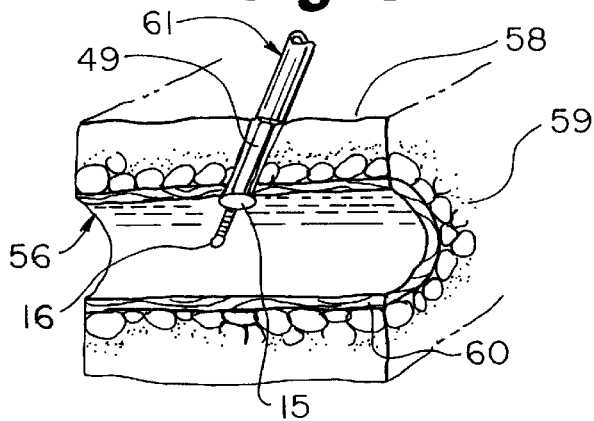
FIG. 3 is a view of the vascular sealing device with its balloon portion inflated, and further showing retraction of the vascular introducer.

Human trials were performed, with various embodiments of the procoagulant, and produced test results as discussed below. The trials included patients undergoing either diagnostic angiograms or interventional procedures, as well as anti-coagulated and non anti-coagulated patients. In each case a vascular sealing device, such as one similar to that described in U.S. Pat. No. 5,626,601 which is hereby incorporated by reference, was used in delivering the procoagulant. Specifically, referring to FIGS. 1–3, the assembly of an uninflated vascular sealing device 10 and a reaccess sheath 49 were first inserted into a standard introducer or vascular sheath 61, which had been previously positioned through a puncture in the skin surface 58, tissue 59, vessel wall 60, and within a blood vessel 56 of a patient for performance of the diagnostic angiogram or interventional procedure. Referring to FIG. 2, the assembly was then advanced by manual manipulation until the distal end 12 of the vascular sealing device extended just beyond the distal end of the introducer 61 and into the blood vessel 56. Fluid was then injected into the vascular sealing device 10 through an inflation port 31 until a predetermined amount of balloon 15 inflation was attained. Next, the vascular sealing device 10 was manually pulled slightly proximally back through the introducer sheath 61 so that the balloon 15 abutted the distal end of the introducer sheath 61. A core wire 17, within the assembly, was also manually, proximally pulled to flatten the profile of the vascular sealing device 10 to minimize disturbance of blood flow in the blood vessel 56. Referring to FIG. 3, the balloon 15 was proximally manipulated to effect a temporary hemostatic seal internal to the blood vessel wall puncture site 57.

Next, the procoagulant was injected through a fluid access port 53 of the introducer sheath 61 and was released out the introducer sheath's distal end at the puncture site 57. The viscosity of the procoagulant substantially maintained the procoagulant locality at the puncture site. After delivery of the procoagulant, the balloon 15 remained abutted against the puncture site 57 while the introducer 61 was retracted. After a predetermined time range, on the order of about 1–3 minutes, the balloon 15 was deflated and the core wire 17 was advanced distally to decrease its profile for removal. The reaccess sheath 49 was advanced distally over the deflated balloon 15 and the combined low profile vascular sealing device-reaccess sheath assembly was proximally removed from the puncture site 57 along with the introducer sheath 61 through the procoagulant.

In each trial, delivery of the procoagulant to the puncture site resulted in the achievement of hemostasis. The time required to achieve hemostasis, i.e. the time that hemostasis is first observed is very rapid, and is clearly less than about 3 minutes from completion of device deployment. A predominant range of time to achieve hemostasis is about 1–3 minutes. Note that this is determined with applying manual or other external compression or suturing. The trials further confirmed that the time to ambulation, which is defined as the time from the end of the procedure to when the patient stands at bedside without rebleeding, is relatively short in comparison with previous techniques. For example, a range of ambulation time is generally about the same time as a routine outpatient full physical examination, i.e. one hour, for non anti-coagulated patients. This would also be a nominal ambulation time for a patient recovering from a diagnostic procedure. Patients who are receiving anticoagulant treatment, or who are recovering from an interventional procedure may experience a longer time to ambulation, as defined above, but will still benefit greatly with a nominal time starting at about two hours. It is recognized that the time to ambulation has multi-factorial dependence, and could be even less than that indicated above.

As the above results indicate, the thrombin and collagen procoagulant of the present invention provides substantial time advantages over manual compression in achieving hemostasis. Further, the avoidance of manual compression and extensive immobilization enhances a patient's comfort and ease in enduring a percutaneous entry procedure. The dramatic human trial results which yielded no intravascular dissemination of procoagulant also provides clear indication of the attendant advantages of this system, method, and materials.

The present invention may be embodied in other specific forms, including alternate delivery means and methods, without departing from the spirit of the essential attributes thereof. For example, certain thrombin batch sizes and sources of supplies may result in different osmolality results. In one embodiment, it is preferable to use a 5,000 unit size supply of thrombin manufactured by Mochida Pharmaceutical Co., Ltd., of Japan. This supply provided advantageous solute factors, and resulted in certain preferred osmolality ranges of the final solution of the procoagulant. In similar manner, the size and concentration of the collagen particles varies by source and by other considerations. This too introduces considerable variability into the viability of the production and use of certain combinations of constituents of the procoagulant, requiring considerable care in such production to achieve consistent and optimal product characteristics. Therefore, the illustrated embodiment should be considered in all respects as illustrative and not restrictive, reference being made to the appended claims rather than to the foregoing description to facilitate determination of the scope of the invention.

What is claimed:

1. A method for closing a puncture or other opening in a blood vessel, comprising the steps of:
   a. inserting an inflatable apparatus through an introducer which is disposed in a blood vessel opening;
   b. inflating the inflatable apparatus;
   c. positioning the inflatable apparatus into contact with the opening sufficient to effect a hemostatic seal at the puncture site;
   d. introducing a liquid procoagulant having a pH of about 5–10 and an osmolality of about 250 to about 450 mOsm/kg to the opening;
   e. deflating the inflatable apparatus; and
   f. removing the inflatable apparatus through the opening and through the procoagulant.

2. A system for closing a puncture or other opening in a blood vessel, comprising:
   a. an inflatable apparatus designed for insertion through an introducer disposed in a blood vessel opening;
   b. an inflatable apparatus configured to permit positioning into contact with the opening sufficient to effect a hemostatic seal at the puncture site; and
   c. a liquid procoagulant having a pH of about 5–10 and an osmolality of about 250 to about 450 mOsm/kg, the procoagulant being designed for precise placement and localization at the opening of the blood vessel external of the vessel lumen and proximal to the inflatable apparatus;
   wherein the system has a low profile when the inflatable apparatus is deflated to facilitate removal of the inflatable apparatus through the opening and through the procoagulant after employment of the apparatus and delivery of the procoagulant.

* * * * *